United States Patent [19]

Dumble

[11] Patent Number: 5,321,043
[45] Date of Patent: Jun. 14, 1994

[54] METHOD OF COMBATTING TRANSPLANT REJECTION

[75] Inventor: Lynette J. Dumble, Victoria, Australia

[73] Assignee: The University of Melbourne, Victoria, Australia

[21] Appl. No.: 986,993

[22] Filed: Dec. 7, 1992

Related U.S. Application Data

[62] Division of Ser. No. 825,669, Jan. 27, 1992, Pat. No. 5,190,972.

[51] Int. Cl.$^5$ ............................................. A61K 31/35
[52] U.S. Cl. ..................................... 514/454; 514/569
[58] Field of Search ................................ 514/454, 569

[56] References Cited

U.S. PATENT DOCUMENTS

| | | | |
|---|---|---|---|
| 4,095,036 | 6/1978 | Yankee | 560/121 |
| 4,205,178 | 5/1980 | Axen | 560/121 |
| 4,239,778 | 12/1980 | Venton et al. | 424/305 |
| 4,306,075 | 12/1981 | Aristoff | 560/56 |
| 4,977,174 | 12/1990 | Stein et al. | 514/382 |

FOREIGN PATENT DOCUMENTS 0347243 12/1989 European Pat. Off. .

OTHER PUBLICATIONS

L. Bowes et al., *Transplantation Proceedings* 21, No. 5, 3769-3770 (1989).
M. Moran et al., *New Eng. J. Med.* 332, No. 17, 1183-1188 (1990).
L. Dumble et al., in Prostaglandins, Leukotrienes, Lipoxins & PAF: XIth Washington International Spring Symposium (Ed. by J. Martyn Bailey) (Abstract 202), (1991).
R. Griepp et al., *Surgery* 81, No. 3, 262-269 (1977).
C. Leithner et al., *Prostaglandins* 22, No. 5, 783-788 (1981).
A. Mirisklavos et al., *Journal of Applied Cardiology* 1, 109-123 (1986).
S. Teraoka et al., *Transplantation Proceedings XIX*, No. 1, 2115-2119 (1987).
B. Uretsky ewt al., *Therapy and Prevention–Cardiac Transplantation* 76, No. 4, 827-834 (1987).
B. Whittle and S. Moncada, *Platelets and Vascular Occlusion*, 72, No. 6, 1219-1225 (1985).
J. Wiederkehr et al., *Aust. N. Z. J. Surg.* 60, 121-124 (1990).
R. Klein et al., in *RU 486 Misconceptions, Myths and Morals* (Spinifex Press, Australia) (Aug. 1991), pp. 82-85, 146-147.
J. Thomson, "Production of Severe Atheroma In A Transplanted Human Heart," *The Lancet* (Nov. 1969), pp. 1088, 1090, 1092.
*Progress in Medicinal Chemistry*, vol. 21 (G. Ellis and G. West Eds.) (Elsevier Science Publishers, B.V.), pp. 238-279 (1984).
F. Mühlbacher et al., *Transplantation Proceedings XIX*, No. 5, 4162-4163 (1987).
N. Redgrave et al., *Transplantation Proceedings* 23, No. 1 (Feb.), 346-347 (1991).

*Primary Examiner*—Marianne M. Cintins
*Assistant Examiner*—John Peabody
*Attorney, Agent, or Firm*—Bell, Seltzer, Park & Gibson

[57] ABSTRACT

The present invention is concerned with methods for the treatment of medical conditions with benzindene prostaglandins. Medical conditions which may be treated by the methods of the present invention include transplant rejection and atherosclerosis.

18 Claims, No Drawings

METHOD OF COMBATTING TRANSPLANT REJECTION

This is a division of Ser. No. 825,669, filed Jan. 27, 1992, now U.S. Pat. No. 5,190,972.

FIELD OF THE INVENTION

The present invention relates to therapeutic methods, in particular combating transplant rejectrion and treating atherosclerosis with certain benzindene prostaglandins.

BACKGROUND OF THE INVENTION

Cyclosporine (CyA; formerly called cyclosporin A) is a cyclic peptide produced by the fungus Tolypocladium inflatum. CyA is an immunosupressant administered to human allogeneic transplant recipients or human subjects undergoing treatment for an autoimmune disease such as myasthenia gravis. A problem with CyA, however, is its organ toxicity. The major toxic side-effect of CyA is nephrotoxicity, but hepatotoxicity and cardiotoxicity have also been noted.

U.S. Pat. No. 4,306,075 describes novel benzindene prostaglandins which produce various pharmacological responses, such as inhibition of platelet aggregation, reduction of gastric secretion, and bronchodilation. It is indicated that the compounds have useful application as anti-thrombotic agents, anti-ulcer agents, and anti-asthma agents. There is no indication that these compounds may be used to combat tissue transplant rejection.

European Patent Application 347243 of A. S. Tadepalli et al. discloses fused-ring prostaglandin derivatives for treating or preventing pulmonary hypertension and for diagnosing primary pulmonary hypertension patients who have active pulmonary vasoconstriction (see also U.S. Pat. No. 5,028,628).

The present invention is based on our ongoing o research into cyclosporine therapies.

SUMMARY OF THE INVENTION

A first aspect of the present invention is a melted for the treatment of a medical condition selected from the group consisting of transplant rejection and atherosclerosis in a subject in need of one or more of such treatments, comprising administering to said subject a therapeutically effective amount of a compound of formula (I):

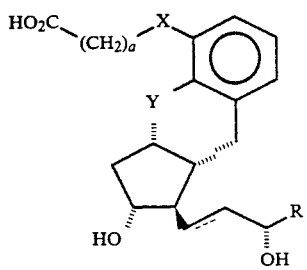

wherein:
a is an integer of from 1 to 3;
X and Y, which may be the same or different, are selected from —O— and —CH$_2$—;
R is —(CH$_2$)$_5$R$^1$ wherein R$^1$ is hydrogen or methyl, or R is cyclohexyl, or R is —CH(CH$_3$)CH$_2$C≡CCH$_3$; and
the dotted line represents an optional double bond;
or a physiologically acceptable salt or acid derivative thereof (i.e., an "active compound").

A second aspect of the present invention is a method of combatting transplant rejection in a subject in need of such treatment. The method comprises concurrently administering the subject an effective transplant-rejection combatting amount of cyclosporine and a compound of formula (I) as given above, or a physiologically acceptable salt or acid derivative thereof, in an amount effective to enhance the activity of the cyclosporine.

A third aspect of the present invention is a method of combatting cyclosporine organ toxicity in a subject in need of such treatment. The method comprises administering said subject an effective cyclosporine organ toxicity-combatting amount of a compound of formula (I) as given above or of a physiologically acceptable salt or acid derivative thereof.

A fourth aspect of the present invention is a method of combatting atherosclerosis (e.g., heart transplant atherosclerosis) in a subject in need of such treatment. The method comprises administering said subject an effective atherosclerosis-combatting amount of a compound of formula (I) as given above or of a physiologically acceptable salt or aid derivative thereof.

Further aspects of the present invention include the use of a compound of formula (I), or a pharmaceutically acceptable salt or acid derivative thereof, for the manufacture of a medicament for combatting transplant rejection, for combatting cyclosporine organ toxicity, and for combatting atherosclerosis.

A further aspect of the present invention is a pharmaceutical formulation comprising cyclosporine in an effective immunosupressive amount and a compound of formula (I) above, or a physiologically acceptable salt or acid derivative thereof, in an amount effective to (a) enhance the activity of cyclosporine, (b) combat cyclosporine organ toxicity or (c) both, together in a physiologically acceptable carrier.

The present invention also provides a method of combatting hyperlipidemia (e.g., cyclosporine immunosupression-induced hyperlipidemia) in a subject in need of such treatment. The method comprises administering said subject an effective hyperlipidemia-combatting amount of a compound of formula (I) as given above or of a physiologically acceptable salt or acid derivative thereof. Also provided is the use of a compound of formula (I) as given above or of a physiologically acceptable salt or acid derivative thereof for the preparation of a medicament for combatting hyperlipidemia.

The benzindene prostaglandins described above have a surprising level of potency in the various therapeutic methods referred to herein. As an advantageous consequence, dosage levels may be kept within a low range (as hereinafter described) when compared to the administration levels of other prostaglandin compounds/analogues. The prostaglandin analogues of this invention do not possess the well known side effects which exist with other prostaglandin compounds/analogues.

Advantages arise from the co-administration of cyclosporine and the benzindene prostaglandins of this invention. Cyclosporine is nephrotoxic, cardiotoxic and hepatotoxic. According to the methods of this invention, less cyclosporine may be administered to a patient when compared with traditional therapies, when the cyclosporine is co-administered or administered in concert with the benzindene prostaglandins (i.e., the active compounds) of this invention due to the synergistic effect between benzindene prostaglandins and cyclosporine in immune suppression.

DETAILED DESCRIPTION OF THE INVENTION

Subjects to be treated by the methods of the present invention are typically human subjects, such as transplant recipients or subjects undergoing treatment for an autoimmune disease such as myasthenia gravis. Transplant recipients may be recipients of kidney, liver, heart, heart-lung, bone-marrow, and cornea transplants. The organ transplant tissue itself is typically human in origin, but may also be from another species such as the rhesus monkey. Where the compound of formula (I) is administered to combat cyclosporine organ toxicity, it may be administered to combat either nephrotoxicity, or hepatotoxicity, but the principle use currently contemplated is in combating nephrotoxicity.

Used alone (and in combination with cyclosporine), the benzindene prostaglandin analogues (i.e., active compounds) described herein reduce the severity of rabbit heart transplant atherosclerosis. Since atherosclerosis, rather than rejection, is the predominant cause of patient death in adult and paediatric heart transplant recipients, the benzindene compounds are useful in preventing this lesion in these patients. Further, since the active compounds described herein are believed to negate the hyperlipidemia induced by cyclosporine immunosupression, they are also contemplated as useful in combatting hyperlipidemia in the general population.

Preferred compounds of formula (I) having particularly desirable properties include those wherein X is 13 O—; Y is —$CH_2$—; and R is —$(CH_2)_4CH_3$.

The term "acid derivative" is used herein to describe $C_{1-4}$ alkyl esters and amides, including amides wherein the nitrogen is optionally substituted by one or two $C_{1-4}$ alkyl groups.

The present invention also includes bioprecursors or "pro-drugs" of the above-defined compounds, that is, compounds which are converted in vivo to compounds of formula (I) or pharmaceutically active derivatives thereof.

A particularly preferred compound of formula (I) above is 9-deoxy-2',9α-methano-3-oxa-4,5,6-trinor-3,7-(1',3'-interphenylene)-13, 14--dihydro-prostaglandin$F_1$ (Compound A), which has the structure of formula (II):

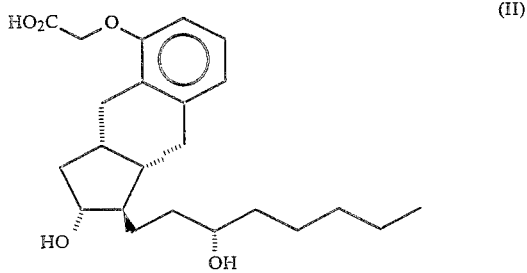

(II)

and pharmaceutically acceptable salts and acid derivatives thereof.

Other compounds useful for practicing the present invention include:
9-Deoxy-2',9α-methano-3-oxa-4,5,6-trinor-3,7-(1',3'-interphenylene)-prostaglandin $F_1$ (Compound B);
9-Deoxy-2',9α-methano-3-oxa-4,5,6-trinor-3,7-(1',3'-interphenylene)-15-cyclohexylprostaglandin $F_1$ (Compound C);
9-Deoxy-2',9α-methano-3-oxa-4,5,6-trinor-3,7-(1',3'-interphenylene)-20-methylprostaglandin $F_1$ (Compound D); and
(15S,16RS)-9-Deoxy-2',9α-methano-16-methyl-3-oxa-18,18,19,19-tetradehydro-4,5,6-trinor -3,7-(1',3'-interphenylene)-prostaglandin $F_1$ (Compound E).

The compounds of the present invention may be prepared in accordance with known techniques, such as methods the same as or analogous to those described in U.S. Pat. No. 4,306,075.

The amount of a compound of formula (I), or a physiologically acceptable salt or acid derivative thereof, which is required in a medication according to the invention to achieve the desired effect will depend on a number of factors, in particular the specific application, the nature of the particular compound used, the mode of administration, and the condition of the patient. In general, a daily dose per patient is in the range 25 μg to 250 mg; typically from 0.5 μg to 2.5 mg, preferably from 7 μg to 285 μg, per day per kilogram bodyweight. For example, an intravenous dose in the range of 0.5 μg to 1.5 mg per kilogram bodyweight per day may conveniently be administered as an infusion of from 0.5 ng to 1.0 μg per kilogram bodyweight per minute. Infusion fluids suitable for this purpose contain, for example, from 10 ng to 10 μg per milliliter. Ampoules for injection contain, for example, from 0.1 μg to 1.0 mg and orally administrable unit dose formulations, such as tablets or capsules, contain, for example, from 0.1 to 100 mg, typically from 1 to 50 mg. In the case of physiologically acceptable salts, the weights indicated above refer to the weight of the active compound ion, that is, the ion derived from the compound of formula (I).

"Concurrently administering" means the compound of formula (I) and the cyclosporine are administered to the subject either (a) simultaneously in time (optionally by formulating the two together in a common carrier), or (b) at different times during the course of a common treatment treatment schedule. In the latter case, the two compounds are administered sufficiently close in time to achieve the intended effect.

Cyclosporine may be administered in a manner and amount as is conventionally practiced. See, e.g., Goodman and Gilman's The Pharmacological Basis of Therapeutics, 1299 (7th ed. 1985). The specific dosage will depend on the condition being treated, the state of the subject, and the route of administration, but will typically be from about 1 to 20 milligrams per kilogram of subject body weight daily, or more preferably from about 1 to 15 milligrams per kilograms body weight daily. For example, cyclosporine may be provided as an oral solution of 100 mg/ml with 12.5% alcohol, and for intraveneous administration as a solution of 50 mg/mL, with 33% alcohol and 650 mg of polyoxyethlated castor oil. For a transplantation subject a typical oral dose is 10 to 15 mg/kg daily, starting a few hours before transplantation and continuing for 1 to 2 weeks, with the dosage then being gradually reduced to a maintenance level of 5 to 10 mg/kg daily. When administered intraveneously, CyA may be given as a dilute solution of 50 mg per 20 to 100 ml of normal saline solution or 5% dextrose in water, by slow infusion over a period of 2 to 6 hours. The intraveneous dose is typically one third of the oral dose. An adrenocorticosteroid such as prednisone is optionally administered with the CyA, as is known in the art.

The present invention extends to non-physiologically acceptable salts of the compounds of formula (I) which may be used in the preparation of the pharmacologically active compounds of the invention. The physiologically acceptable salts of compounds of formula (I) include salts derived from bases. Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

In the manufacture of a medicament according to the invention, hereinafter referred to as a "formulation," the compounds of formula (I) and the physiologically acceptable salts thereof, or the acid derivatives of either thereof (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients such as cyclosporine and (optionally) an adrenocorticosteroid such as prednisone.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or moulding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1 to 5% w/v of active compound and are administered at a rate of 0.1 ml/min/kg.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, for example, Pharmaceutical Research 3 (6), 318, (1986)) and typically take the form of an optionally buffered aqueous solution of the active compound. Suitable formulations comprise citrate or bis/tris buffer (pH 6) or ethanol/water and contain from 0.1 to 0.2M active ingredient.

The present invention is explained in greater detail in the following Examples.

EXAMPLE 1

In Vitro Comparison of the Immunosuppressive Potential of Synthetic Prostaglandin Analogues Heparinised blood was obtained from five healthy donors without history of previous blood transfusion, pregnancy, or organ transplantation.

Sandimmun (Sandoz Ltd. Basel, Switzerland) Cyclosporine (CyA) at 50 mg/mL was diluted in physiological saline to concentrations of 1.0-0.001 μg/mL.

Prostaglandin (PG) analogues $PGE_1$, $PGE_2$, $PGF_{2a}$, and $PGI_2$ were supplied by the Upjohn Company (Kalamazoo, Mich.) in the form of 15-(s)-15-methyl $PGE_1$, 16,16-dimethyl $PGE_2$, 16,16-dimethyl $PGF_{2a}$, and 9-deoxy-2,9a-methano-3-oxa-4,5,6-trinor-3,7-(1', 3'-interphenylene)-13,14'-dihydroprostaglandin FI (Compound A). Each was provided in methyl acetate at 10 mg/mL that was subsequently diluted, first with ethyl alcohol to a concentration of 1 mg/mL and thereafter with physiological saline to the concentration range required for the study, 10.0-0.001 μg/mL.

Responder lymphocytes were isolated from the healthy donor heparinised blood by density gradient separation and suspended in glutamine, antibiotic-supplemented RPMI medium containing 10% autologous responder lymphocyte donor serum at a concentration of $1 \times 10^6$ cells/mL. The stimulator population consisted of Epstein-Barr virus (EBV)-transformed lymphoblastoid cells that were irradiated (130 Gy) before suspension also at $1 \times 10^6$ cells/mL in glutamine, antibiotic-supplemented RPMI medium that contained 10% autologous responder lymphocyte donor serum.

Equal volumes (0.1 mL) of responder and stimulator cells were incubated in triplicate wells of microtitre trays with each of the following:
1. 0.05 mL of medium
2. 0.025 mL of medium plus 0.025 mL of serial dilutions of CyA or $PGE_1$, $PGE_2$, $PGF_{2a}$, or $PGI_2$;
3. 0.025 mL of serial dilutions of CyA plus 0.025 mL of serial dilutions of $PGE_1$, $PGE_2$, $PGF_{2a}$, or $PGI_2$.

Following incubation at 37° C. (5% $CO_2$) for 4 days, 1.0 mCi of tritiated thymidine was added to all cultures before further incubation for 6-8 hours, after which cells were automatically harvested (Skatron, Liebyen, Norway) on Titertek filter paper (Flow Laboratories, Irvine, Scotland) that was placed in vials containing liquid scintillation fluid for counting in a Beckman beta counter (Beckman, Brea, Calif.). Triplicate MLC responses from responder-, stimulator-, and drug-containing cultures were compared with triplicate responses from cultures containing 0.05 mL of medium as a substitute for the appropriate drugs to maintain constant culture volume, in order to determine the minimum concentrations of CyA, $PGE_1$, $PGE_2$, $PGF_{2a}$, and $PGI_2$ which alone induced 50% MLC inhibition and the minimum concentrations of CyA plus $PGE_1$, $PGE_2$, $PGF_{2a}$, or $PGI_2$ which induced the same degree of inhibition.

The percent MLC inhibition induced by CyA and the PG analogues as single agents is shown in Table 1. The most potent MLC suppression, on a milligram for milligram basis, was obtained from CyA and $PGI_2$ which each induced 50% inhibition at a minimum concentration of 0.1 μg/mL. The $PGE_1$ and $PGE_2$ analogues induced the same degree of inhibition from 10 times greater concentrations, 1.0 μg/mL, while 50% inhibition due to $PGF_{2a}$ was only achieved with a concentration of 10.0 μg/mL.

Table 2 shows the effect of CyA combined with each of the PG analogues on the MLC response. The inhibition induced by CyA and the PGE analogues indicates a similar degree of synergy from CyA and PGE, or CyA and $PGE_2$ with the 50% level achieved with CyA at 0.01 μg/mL and $PGE_1$ or $PGE_2$ at 0.01 μg/mL. CyA and $PGF_{2a}$ suppression of the MLC indicates that the combined action has no influence further than that exerted when each was added alone to cultures as 50% MLC suppression was observed only from cultures that contained at least 0.1 μg/mL CyA or 10.0 μg/mL $PGF_{2a}$. The inhibition induced by CyA and $PGI_2$ combinations indicates a synergy that parallels that observed between CyA and the PGE analogues. The 50% level was obtained with CyA at 0.01 μ/mL and $PGI_2$ at 0.01 μg/mL.

TABLE 1

Suppression of MLC Responses by CyA, $PGE_1$, $PGE_2$, $PGF_{2a}$ and $PGI_2$

| Agent | Concentration, μg/mL* | | | | |
|---|---|---|---|---|---|
| | 0.001 | 0.01 | 0.1 | 1.0 | 10.0 |
| CyA | 11 | 25 | 52 | 72 | 84 |
| $PGE_1$ | 5 | 18 | 36 | 56 | 61 |
| $PGE_2$ | 6 | 18 | 32 | 51 | 58 |
| $PGF_{2a}$ | 0 | 4 | 16 | 29 | 50 |
| Prostacyclin | 10 | 22 | 51 | 61 | 77 |

*Mean % (mean calculated from % decreases obtained in MLCs of five healthy, nonsensitised donors) decrease of cpm in drug-containing cultures compared with cpm (mean cpm in drug-free cultures = 29 414) in drug-free cultures.

These results indicate that each of the PG analogues has the potential to suppress the in vitro lymphoid response to alloantigens. However, the concentrations of each analogue that are required to suppress that response differ significantly, with $PGI_2$ being 10 times more effective than $PGE_1$ and $PGE_2$, and the PGE analogues being a further 10 times more effective than the $PGF_{2a}$ analogue which showed no indication of synergistic interaction with CyA.

In combination with CyA, the $PGI_2$, $PGE_1$ and $PGE_2$ analogues promote even greater immunosuppressive activity. Fifty percent suppression of the MLC was obtained with CyA at 0.01 μg/mL when combined with $PGI_2$ at 0.01 μg/mL, which is a 10-fold decrease in the concentration of each that was necessary to achieve the same degree of suppression when either was used alone. Similarly, CyA and $PGE_1$ or $PGE_2$ combinations are effective in the induction of 50% MLC suppression with a 10-fold decrease in the concentration of CyA but a 100-fold decrease in PGE concentration. These results suggest that the PGE and $PGI_2$ derivatives may have CyA sparing potential.

TABLE 2

Suppression of MLC Responses by CyA in Combination with PG Analogues

| PG Analogue (μg/mL) | | CyA Concentration (μg/mL)* | | | | |
|---|---|---|---|---|---|---|
| | | 0.001 | 0.01 | 0.1 | 1.0 | 10.0 |
| $E_1$ | 0.01 | 22 | 52 | 64 | 74 | 86 |
| | 0.1 | 20 | 51 | 64 | 74 | 83 |
| | 1.0 | 59 | 62 | 70 | 79 | 84 |
| | 10.0 | 62 | 67 | 72 | 82 | 85 |
| $E_2$ | 0.01 | 23 | 49 | 55 | 63 | 68 |
| | 0.1 | 26 | 52 | 58 | 66 | 70 |
| | 1.0 | 58 | 56 | 67 | 80 | 85 |
| | 10.0 | 60 | 71 | 72 | 88 | 86 |
| $F_{2a}$ | 0.01 | 14 | 25 | 55 | 70 | 86 |
| | 0.1 | 14 | 24 | 55 | 72 | 86 |
| | 1.0 | 31 | 30 | 58 | 76 | 85 |
| | 10.0 | 58 | 65 | 69 | 79 | 86 |
| $I_2$ | 0.01 | 27 | 58 | 75 | 86 | 87 |
| | 0.1 | 68 | 76 | 86 | 85 | 85 |
| | 1.0 | 81 | 85 | 85 | 85 | 88 |
| | 10.0 | 86 | 88 | 85 | 86 | 86 |

EXAMPLE 2

Synergistic Prolongation of Rabbit Renal Allograft Survival

This study was performed to assess the effectiveness of Compound A as an immunosuppressive agent in a rabbit renal allograft model.

Left orthotopic renal transplantation was performed from New Zealand White rabbit donors into Anglo lop-ear recipients. See D. Francis et al., *Aust. N. Z. J. Surgery* 60, 45, 1990. Contralateral nephrectomy and graft biopsy were performed on the first post-operative day. Each recipient was subsequently dependent on its transplant for renal function. Serum creatinine (sCr) was measured every 48 hours and animals were culled once sCr had risen above 1.2 mMoles/1, taken as an arbitrary end-point representing graft failure. Graft biopsies were performed weekly and post-mortem to ensure that graft loss was secondary to rejection. Standard haematoxylin and eosin and Masson's trichrome stains were performed.

Compound A was provided as a powder which was dissolved in absolute ethanol to yield a 1 mg/ml solution. 50 μg/kg/day was administered subcutaneously for seven days commencing perioperatively. Ethanol (50 μl/kg/day) was administered in vehicle-only control animals. CyA (Sandimmun, Sandoz Ltd. Switzerland) was administered intravenously as a single perioperative dosage of 20 or 5 mg/kg. Blood CyA levels were measured 24 hours post-dosage (Abbott TDX fluorescence immunoassay).

The transplant groups and their survival results are shown in Table 3. Compound A prolonged allograft survival over that of untreated animals, but this survival prolongation was not significantly different from that observed with ethanol vehicle alone. However, Compound A and CyA synergistically enhanced graft survival, whereas CyA and ethanol did not. No CyA-sparing effect was demonstrated when Compound A and 5 mg/kg of CyA, which did not prolong graft survival alone, were administered together. Histological assessment revealed that the pattern of graft infiltrate during acute rejection was not different between groups. Cyclosporine levels were not significantly different between treatment groups (270 ng/ml, median group 3; 264 ng/ml, median group 4).

TABLE 3

Survival of Renal Allografts in Rabbits Treated with Compound A, Ethanol Vehicle and/or CyA

| Group* | Treatment | Graft Survival (d) | Median Graft Survival (d) |
|---|---|---|---|
| 1 | nil | 7, 9, 9, 10, 10, 13 | 9.5 |
| 2 | Compound A | 13, 13, 13, 14, 15, 21 | 13.5 |
| 3 | CyA (20 mg/kg) | 9, 12, 13, 20, 26, 38 | 16.5 |
| 4 | Compound A + CyA (20 mg/kg) | 20, 23, 26, 26, 31, 35, 43 | 26 |
| 5 | CyA (5 mg/kg) | 7, 8, 10, 10, 11, 12, 15 | 10 |
| 6 | Compound A + CyA (5 mg/kg) | 13, 14, 14, 15, 17, 19, 27 | 15 |
| 7 | Ethanol | 8, 11, 12, 13, 18, 18 | 12.5 |
| 8 | Ethanol + CyA (20 mg/kg) | 10, 10, 11, 11, 14, 19 | 11 |

*1 vs 2, P < .005; 3 vs 4, P < .05; 1 vs 5, NS; 2 vs 6, NS; 2 vs 7, NS, 4 vs 8, P < .005 (Mann-Whitney U tests).

EXAMPLE 3

Prevention of Acute Cyclosporine (CyA) Nephrotoxicity in Rabbits

New Zealand White rabbits were studied in three treatment groups: (1) CyA alone; (2) CyA and Compound A: and (3) CyA and ethanol vehicle.

CyA (Sandimmun, Sandoz Ltd. Switzerland) was administered by slow intravenous injection, 100 mg/kg/day, for seven days. Compound A was provided as a powder which was dissolved in absolute ethanol to yield a mg/ml solution. 50 ug/kg/day was administered subcutaneously for seven days. Ethanol (50 ul/kg/day) was administered in vehicle-only control animals. Blood CyA levels were measured 24 hours following completion of a seven days treatment (Abbott TDX fluorescence immunoassay).

Serum creatinine (Cr) and urea were measured prior to commencement of treatment (day 0) and 24 hours following treatment (day 7). Day 7 renal biopsies were stained with haematoxylin and eosin and Masson's trichrome. Results are shown in Table 4.

TABLE 4

Serum creatinine and urea in Rabbits Treated with High Dose CyA ± Compound A or Ethanol

| Group | Treatment | Mean Cr/Urea Day 0 (mMoles/l) | Mean Cr/Urea Day 7 (mMoles/l) | Mean Cr/Urea Change | Mean CyA Level (ng/ml) |
|---|---|---|---|---|---|
| 1 | CyA (n = 4) | 0.05/6.5 | 0.11/13.5 | $+0.06^a/+7^b$ | 860 |
| 2 | CyA + Compound A (n = 4) | 0.08/5.9 | 0.07/5.7 | $-0.01^a/-0.2^b$ | 713 |
| 3 | CyA + Ethanol (n = 4) | 0.07/9 | 0.14/26 | $+0.07^a/+17^b$ | 607 |

$^a$Group 1 or 3 vs 2, P < 05;
$^b$Group 1 or 3 vs 2, P < 05 (Mann-Whitney U test).

Consistent nephrotoxicity was observed in rabbits treated with 100 mg/kg/day of CyA. However, treatment was associated with 60% mortality and 7–10% weight loss. Irrespective of the treatment group, Compound A had a significant protective effect on renal function, as measured by serum Cr and urea. Blood CyA levels were not significantly different between treatment groups. Histology revealed isometric tubular vacuolation in all but one renal biopsy (a group 2 rabbit). Hypertrophy of the juxtaglomerular apparatus was observed in 50% of rabbits, irrespective of the treatment group.

PGE$_2$ analogue is reported to reduce CyA nephrotoxicity in rats, see L. Makowka et al., *Clinical Nephrology* 25 (Suppl. 1), 589 (1986); and B. Ryffel et al., *Transplant Proc.* 18, 626 (1986); however, in these studies CyA was administered anterally and CyA absorption was impaired by the PG analogue, confounding interpretation of the results. See B. Ryffel et al., *Transplant Proc.* 18, 626 (1986). In this study, CyA was administered parenterally and a PGI$_2$ analogue conferred significant protective affect on renal function without effecting CyA bioavailability. Histological tubular toxicity (tubular vacuolation), which is not of functional significance, see H. Dieperink, *Danish Medical Bulletin* 36, 235 (1989), was not prevented by Compound A. Hypertrophy of the juxtaglomerular apparatus may be a physiological response to inanition and dehydration. See G. Thiel, *Clinical Nephrology* 25 (Suppl. 1), 5205 (1986).

The foregoing examples are illustrative of the present invention, and are not to be construed as limiting thereof. The invention is defined by the following claims, with equivalents of the claims to be included therein.

That which is claimed is:

1. A method of combatting transplant rejection in a subject in need of such treatment, comprising concurrently administering said subject an effective transplant-rejection combatting amount of cyclosporine and a compound of formula (I):

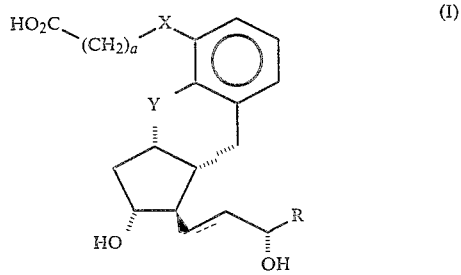

wherein:
 a is an integer of from 1 to 3;
 X and Y, which may be the same or different, are selected from —O— and —CH$_2$—;
 R is —(CH$_2$)$_5$R$^1$ wherein R$^1$ is hydrogen or methyl, or R is cyclohexyl, or R is —CH(CH$_3$)CH$_2$C≡CCH$_3$; and
 the dotted line represents an optional double bond;
 or a physiologically acceptable salt or acid derivative thereof;
 the compound of formula (I) being administered in an amount effective to enhance the activity of cyclosporine.

2. A method according to claim 1, wherein said administering step is an oral administration step.

3. A method according to claim 1, wherein said administering step is a parenteral administration step.

4. A method according to claim 1, wherein said administering step is a transdermal administration step.

5. A method according to claim 1, wherein said administering step is a transdermal iontophoresis administration step.

6. A method according to claim 1, wherein said subject is the recipient of an organ tissue transplant, said organ tissue selected from the group consisting of kidney, liver, heart, lung, bone marrow, and cornea tissue.

7. A method of combatting transplant rejection in a subject in need of such treatment, comprising concurrently administering said subject an effective transplant-rejection combatting amount of cyclosporine and a compound of formula (I):

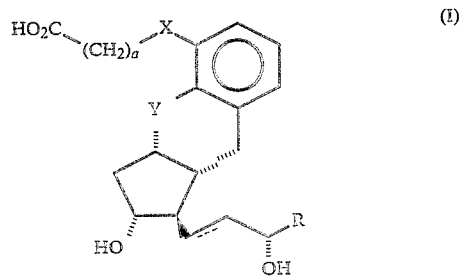

wherein:
 a is an integer of from 1 to 3;
 X is —O—;
 Y is —CH$_2$—;
 R is —(CH$_2$)$_4$CH$_3$; and
 the dotted line represent an optional double bond;
 or a physiologically acceptable salt or acid derivative thereof;
 the compound of formula (I) being administered in an amount effective to ehance the activity of cyclosporine.

8. A method according to claim 7, wherein said administering step is an oral administration step.

9. A method according to claim 7, herein said administering step is a parenteral administration step.

10. A method according to claim 7, wherein said administering step is a transdermal administration step.

11. A method according to claim 7, wherein said administering step is a transdermal iontophoresis administration step.

12. A method according to claim 7, wherein said subject is the recipient of an organ tissue transplant, said organ tissue selected from the group consisting of kidney, liver, heart, lung, bone marrow, and cornea tissue.

13. A method of combatting transplant rejection in a subject in need of such treatment, comprising concurrently administering said subject an effective transplant-rejection combatting amount of cyclosporine and 9-deoxy-2', 9α-methano-3-oxa-4,5,6-trinor-3,7-(1',3'-interphenylene)-13, 14-dihydroprostaglandin F$_1$, or a physiologically acceptable salt or acid derivative thereof, in an amount effective to enhance the activity of cyclosporine.

14. A method according to claim 13, wherein said administering step is an oral administration step.

15. A method according to claim 13, wherein said administering step is a parenteral administration step.

16. A method according to claim 13, wherein said administering step is a transdermal administration step.

17. A method according to claim 13, wherein said administering step is a transdermal iontophoresis administration step.

18. A method according to claim 13, wherein said subject is the recipient of an organ tissue transplant, said organ tissue selected from the group consisting of kidney, liver, heart, lung, bone marrow, and cornea tissue.

* * * * *

UNITED STATES PATENT AND TRADEMARK OFFICE
CERTIFICATE OF CORRECTION

PATENT NO. : 5,321,043
DATED : June 14, 1994
INVENTOR(S) : Lynette J. Dumble

It is certified that error appears in the above-indentified patent and that said Letters Patent is hereby corrected as shown below:

Column 1, line 45, please correct " melted " to read
-- method --.

Column 2, line 29, please correct " aid " to read
-- acid --.

Column 3, lines 38 & 39, please correct " 130- " to read
--0--.

Column 4, line 13, please correct " trinor    -3, " to read
-- trinor -3,7- --.

Column 10, line 31, please correct " mg/ml " to read
-- 1 mg/ml --.

Signed and Sealed this

Twenty-fifth Day of October, 1994

Attest:

BRUCE LEHMAN

Attesting Officer     Commissioner of Patents and Trademarks